(12) United States Patent
Mialhe

(10) Patent No.: US 7,708,253 B2
(45) Date of Patent: May 4, 2010

(54) VALVE FOR A SURGICAL OR MEDICAL INSTRUMENT

(76) Inventor: Claude Mialhe, 292 Chemin de la Sirene, Draguignan (FR) F-83300

( * ) Notice: Subject to any disclaimer, the term of this patent is extended or adjusted under 35 U.S.C. 154(b) by 344 days.

(21) Appl. No.: 11/791,713

(22) PCT Filed: Dec. 2, 2005

(86) PCT No.: PCT/EP2005/056440

§ 371 (c)(1),
(2), (4) Date: May 29, 2007

(87) PCT Pub. No.: WO2006/061356

PCT Pub. Date: Jun. 15, 2006

(65) Prior Publication Data

US 2008/0009834 A1  Jan. 10, 2008

Related U.S. Application Data

(60) Provisional application No. 60/669,361, filed on Apr. 8, 2005.

(30) Foreign Application Priority Data

Dec. 6, 2004  (FR)  .................................. 04 52874

(51) Int. Cl.
*F16K 7/04*  (2006.01)
(52) U.S. Cl. ............................. 251/4; 251/294; 604/171
(58) Field of Classification Search ...................... 251/4, 251/90, 294; 604/171
See application file for complete search history.

(56) References Cited

U.S. PATENT DOCUMENTS

| 4,412,669 | A | * | 11/1983 | Hanyu et al. | .................. 251/4 |
| 4,523,737 | A | * | 6/1985 | Wentworth | .................. 251/4 |
| 4,540,411 | A | | 9/1985 | Bodicky | |
| 4,872,365 | A | * | 10/1989 | Wolf | .................. 74/501.6 |
| 5,158,553 | A | | 10/1992 | Berry et al. | |
| 5,197,955 | A | | 3/1993 | Stephens et al. | |
| 5,211,370 | A | | 5/1993 | Powers et al. | |
| 5,256,150 | A | | 10/1993 | Quiachon et al. | |
| 5,350,364 | A | | 9/1994 | Stephens et al. | |
| 5,484,418 | A | | 1/1996 | Quiachon et al. | |
| 6,221,057 | B1 | | 4/2001 | Schwartz et al. | |
| 6,652,492 | B1 | * | 11/2003 | Bell et al. | .............. 604/167.01 |
| 6,808,520 | B1 | | 10/2004 | Fourkas et al. | |
| 2003/0116731 | A1 | | 6/2003 | Hartley | |
| 2004/0178586 | A1 | | 9/2004 | Junge | |

FOREIGN PATENT DOCUMENTS

| EP | 0 550 069 | 7/1993 |
| WO | 03/048616 | 6/2003 |
| WO | 2005/058409 | 6/2005 |

\* cited by examiner

*Primary Examiner*—John K Fristoe, Jr.
(74) *Attorney, Agent, or Firm*—Young & Thompson

(57) ABSTRACT

A valve for surgical or medical instruments includes a passage that can be at least partially sealed by twisting a flexible section (1) of the passage wall, an element for rotating a mobile end (3) of flexible section (1), characterized in that the actuating element includes a cable for transmitting movement to mobile end (3) of the flexible section. Also described is a surgical or medical instrument including a valve as detailed.

19 Claims, 7 Drawing Sheets

VALVE FOR A SURGICAL OR MEDICAL INSTRUMENT

CROSS-REFERENCE TO RELATED APPLICATIONS

The present application claims benefit of priority and incorporates by reference French Application No. 0452874 filed Dec. 6, 2004, U.S. Application 60/669,361 file Apr. 8, 2005 and PCT/EP2005/056440 filed Dec. 2, 2005.

STATEMENT REGARDING FEDERALLY SPONSORED RESEARCH OR DEVELOPMENT

None.

THE NAMES OF THE PARTIES TO A JOINT RESEARCH AGREEMENT

None.

INCORPORATION-BY-REFERENCE OF MATERIAL SUBMITTED ON A COMPACT DISC

None.

BACKGROUND OF THE INVENTION

1. Field of the Invention

This invention concerns a valve for surgical or medical instrument as well as a surgical or medical instrument equipped with the said valve.

The invention will particularly apply to the execution of endovascular introducers.

2. Description of Related Art

However, this field is not exhaustive.

Instruments used as introducers into a patient's body, and in particular for endovascular, including percutaneous and/or transparietal, interventions require the presence of parts that will ensure that the introducer creates a seal.

More especially, the invention applies when introducing objects such as elongated surgical guides, balloons and endoprostheses into the instrument to avoid as far as possible the backflow of blood through the introducer instrument.

Document U.S. Pat. No. 5,256,150 describes a device for introducing catheters into a vessel in the patient's body.

This device applies to a large-diameter system with a cylindrical deformable sheath made of a flexible material that is capable of being twisted by the relative rotation of these two ends.

This deformation is induced by rotating one of the ends using a complex drive system which includes a rack and a system of toothed wheels.

This system does not give entire satisfaction, especially because the system used by the operator to transmit the movement to the cylindrical element which can be twisted is complex and this leads to high manufacturing costs and a bulky product.

The present invention overcomes entirely or in part the disadvantages of current devices and presents an alternative to the known means of actuation.

One of the advantages of the invention is to develop a valve system which is notably less expensive than the existing one and much smaller.

The size of the operating assembly is particularly important as the larger the system, the less ergonomic it becomes.

BRIEF SUMMARY OF THE INVENTION

According to one embodiment, the configuration of the valve according to the invention allows it to be operated by an operator using only one hand, the hand which he uses to hold the surgical instrument itself.

According to a preferred variant, the invention also allows smooth rotational movement of a torsionally deformable element.

In addition, the cable drive system proposed according to the preferred embodiment enables the gripping means to be positioned and oriented in a very flexible manner depending on needs in terms of ease of use.

Moreover, the invention can be perfectly adapted to the size of the introduced element so as to ensure this element forms an excellent seal.

In particular, the system allows the user positioned longitudinally relative to the valve to operate the invention.

This produces natural actuation.

The invention concerns a valve for a surgical or medical instrument comprising:

a passage that can be at least partially closed by torsional deformation of a flexible section of the passage wall, means for rotating a mobile end of flexible section in order to generate torsion, characterized in that the actuation means comprise a cable for transmitting movement to the mobile end of flexible section.

According to non exhaustive but advantageous variants, this valve is such that:

one end of the transmission cable is secured to gripping means which can be moved by an operator.

it comprises an angle drive device to deviate the transmission cable.

the angle drive consists of a pulley.

the angle drive and gripping means are arranged so that gripping means can be moved along the longitudinal axis of the valve.

it has means for returning mobile end to the default position.

the return means consist of a torsional spring the end of which is fixed and whose other end acts in rotation with mobile end of flexible section.

the return means are arranged so that the passage of the valve is closed by default.

it includes means for blocking the valve in the open position.

the blocking means include a pin blocking the actuating means mobile end acts in rotation with a rotational shaft to which is fastened one end of the transmission cable.

rotary shaft has a groove for fastening and winding up the transmission cable.

It includes an additional cable which, when pulled, is capable of transmitting a movement to mobile end of flexible section in the opposite direction to that of the transmission cable.

the additional cable is guided by a return pulley and an angle drive pulley.

the mobile end acts in rotation with rotary shaft which has a groove for fastening and winding up the transmission cable and an additional groove for fastening and winding up additional cable.

the gripping means move in a slide the edges of which have at least one row of teeth for retaining a finger assembled elastically on the gripping means.

This present invention also relates to a medical and surgical instrument equipped with such a valve.

Other applications and advantages will appear during the description of a preferred embodiment which follows, but which is not exhaustive.

BRIEF DESCRIPTION OF THE SEVERAL VIEWS OF THE DRAWING

The attached drawings are given as examples and are not an exhaustive representation of the invention. They represent only one embodiment of the invention and will help to make it easily understood.

FIGS. 6 to 9 show in turn certain components of the valve subject of the invention.

Thus, FIG. 6 shows a pulley that can be used as an angle drive.

FIG. 7 shows an example of the valve body configuration.

FIG. 8 shows a possible arrangement of the gripping means.

FIG. 9 shows an embodiment of the rotary shaft in perspective view showing more particularly the front and a view showing more particularly the rear of the shaft.

Figure 14:
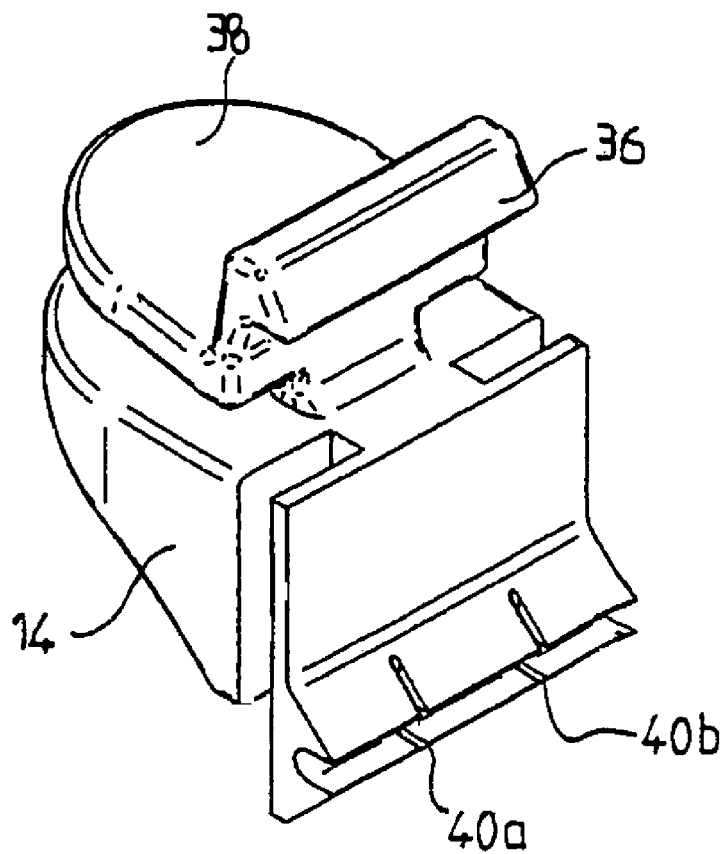
FIG. 14 shows a configuration of a gripping means used to fasten one end of the cables.
Figure 15:
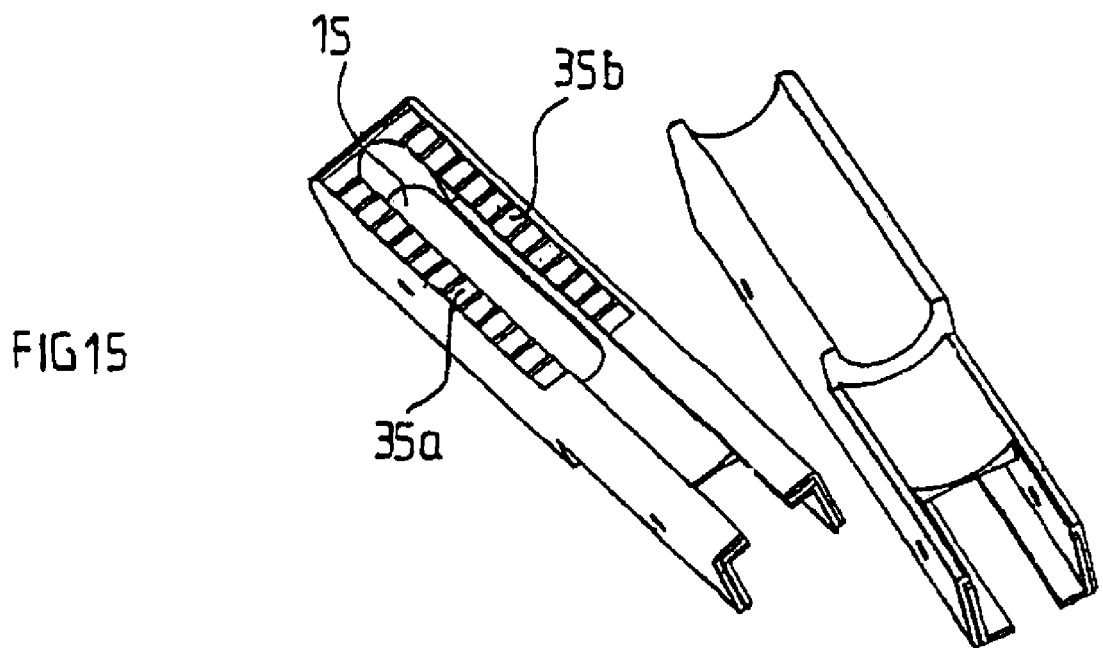

A slide for the gripping means in FIG. 14 is shown on FIG. 15.

DETAILED DESCRIPTION OF THE INVENTION

The valve according to the invention uses the twisting properties of a flexible section 1 of a passage inside the valve.

This passage extends generally along the length of the valve so as to emerge in tube 5, a distal part of which is used for introduction into the patient's body.

Figure 1:
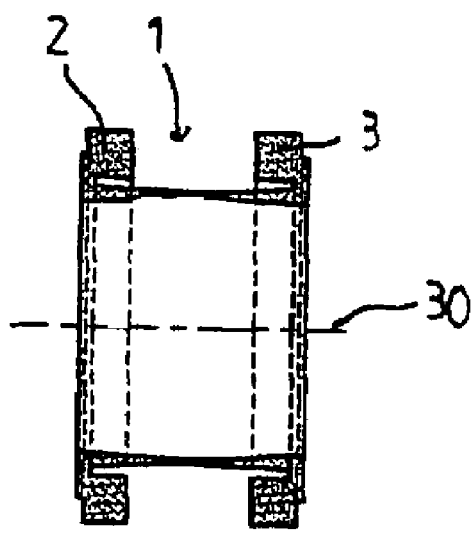
FIGS. 1 to 3 show the flexible section of the valve in three configurations with torsional mechanical stress.
Figure 2:
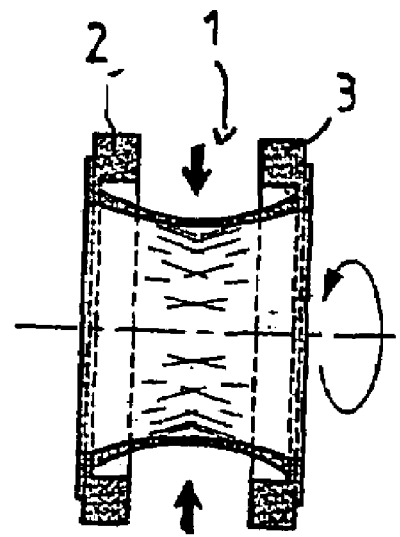
Figure 3:
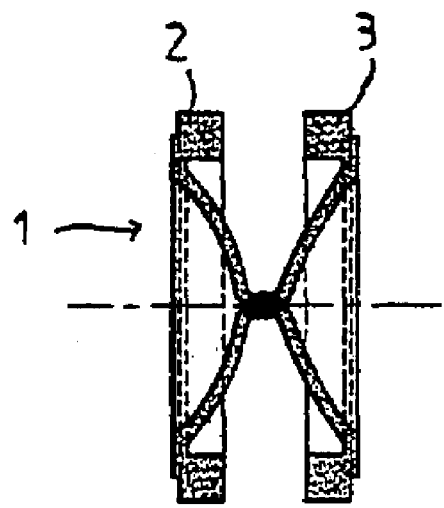

The flexible section such as is shown on FIGS. 1 to 3 is made up of an appreciably hollow cylindrical form made of a tight and flexible material such as silicone.

Section 12 in this case includes two ends 2, 3 with an edge which is thicker than the remainder of flexible section 1 so as to constitute elements joining the flexible section to the other parts.

On FIG. 1, flexible section 1 is not stressed and the central passage is entirely open.

On FIG. 2, an arrow along the valve axis indicates the start of end 3 rotation and, therefore, the start of flexible section 1 tending to create a constricted zone roughly in the middle of flexible section 1, as show the arrows oriented vertically.

FIG. 3 shows another configuration of flexible section 1 in which torsion has continued to be applied so as to completely close the passage at the centre of flexible section 1.

The means for rotating end 3 of flexible section 1 will now be more practically explained in greater detail.

It will be noted that the example here executes rotation of end 3.

However, it could be another end.

Moreover, the simultaneous and opposite rotation of two ends 2, 3 is not excluded by the invention.

Figure 4:
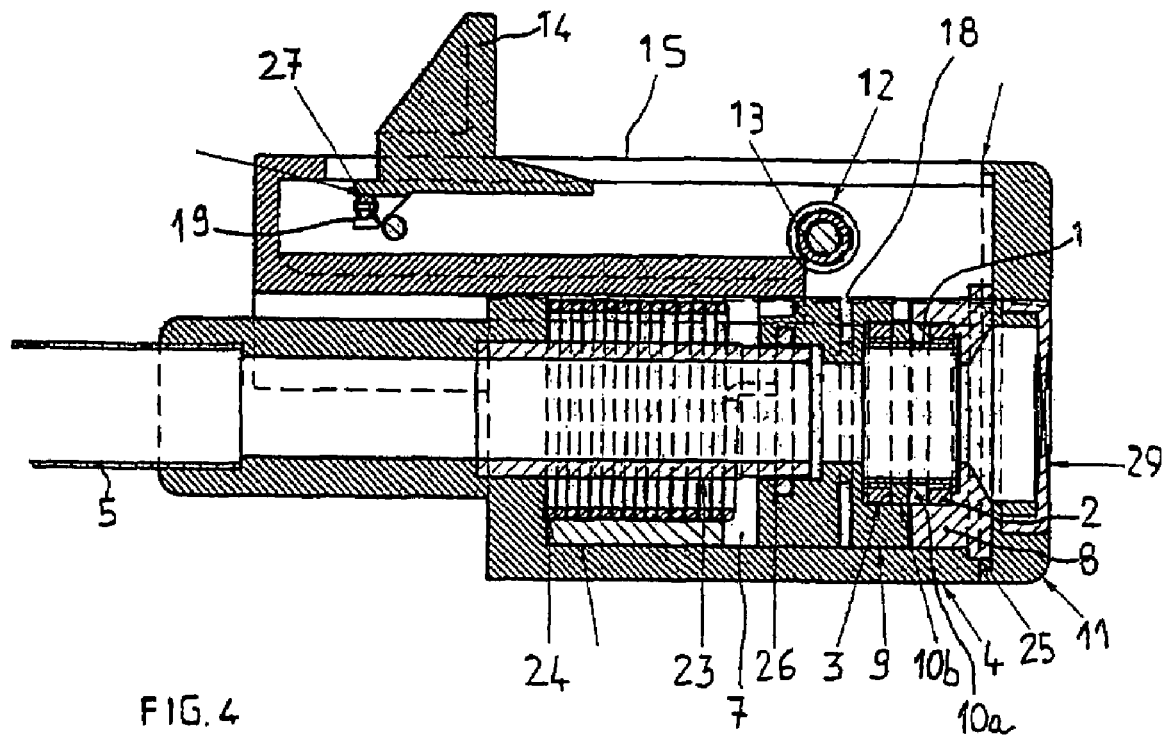
FIG. 4 is a sectional view B-B of FIG. 5 showing the longitudinal elements comprising the valve.

FIG. 4 shows a preferred embodiment of the means for rotating end 3 of flexible section 1 using a cable.

On this figure, the passage in the centre of the valve is closed so as to constitute the default position of the system.

On this figure, end 3 of flexible section 1 is turned by default so as to twist flexible section 1.

The operator is able to turn end 3 in the opening direction when it is required to introduce an object through the valve.

In the illustrated example, end 3 acts in rotation with a rotary shaft 9 shown on FIG. 4 and illustrated in greater detail on FIG. 9.

End 3 is received on front face 21 of rotary shaft 9 and is fixed by an internal ring 10b applied against the edge of end 3.

This assembly is shown on FIG. 4.

In a relatively similar manner, end 2 acts with fixed ring 8 receiving end 2 on one of its faces onto which is positioned an internal ring 10b so as to block it by its edge.

In the example shown, end 2 is situated at the proximal end of the valve.

The assembly is housed in a body 4, for example made of moulded plastic and closed by a cover 11, preferably equipped with a seal 25 to ensure tight closure of the assembly.

Seal 25 includes a central cut-out to allow the passage of objects and their centering.

However, this seal is not perfect and is maximized by the one produced by flexible section 1.

Rotary shaft 9 rotates end 3 of flexible section 1. This shaft 9 is itself driven by a cable not shown, moved by gripping means 14, in this case in the form of a pull-device which is capable of moving along the longitudinal axis of the valve.

Figure 5:
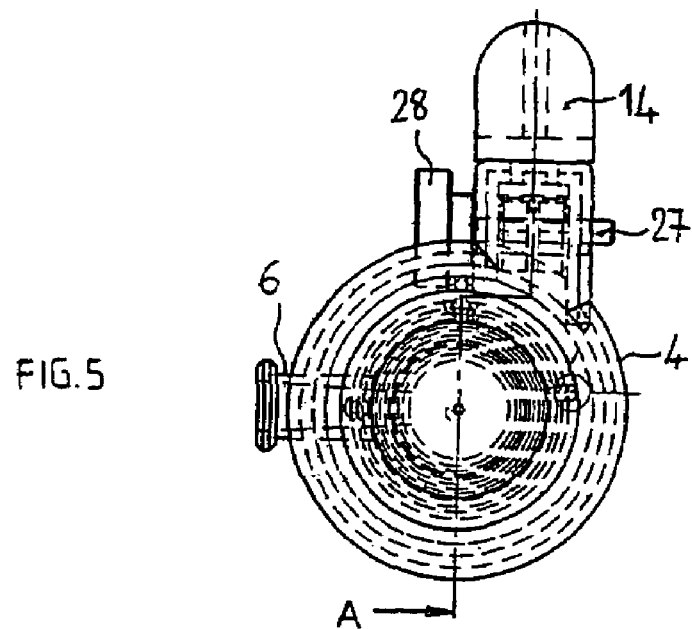
FIG. 5 is a side view of the invention.
Figure 6:
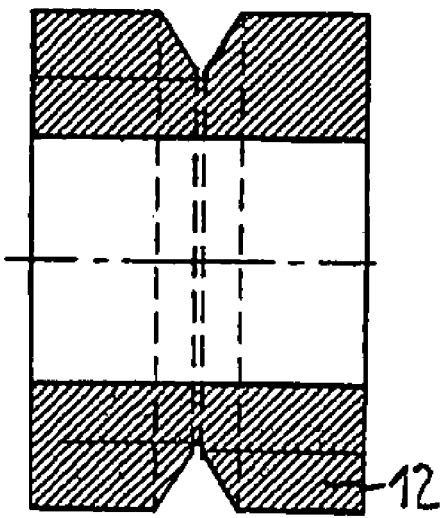
Figure 8:
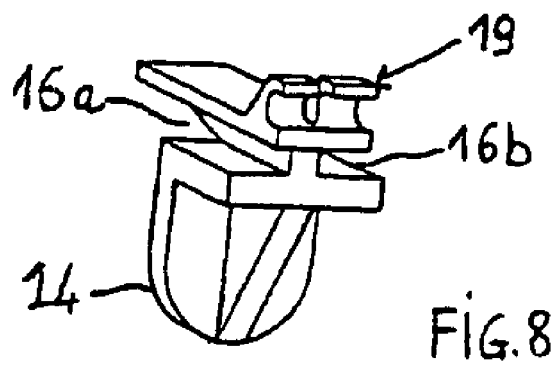

Gripping means 14 shown on FIGS. 4, 5 and 8 show a part to be gripped by the user, a fastening zone 19 allowing one end of the cable and an intermediate part equipped with two grooves 16a, 16b to be joined together so as to act with slide 15 formed longitudinally on a side section of body 4.

The side section constituting the slide may consist of a single part in body 4 or take the form of an added part.

The slide includes an opening, the longitudinal edges of which allow the engagement of grooves 16a, 16b and the sliding movement of gripping means 14.

Figure 7:
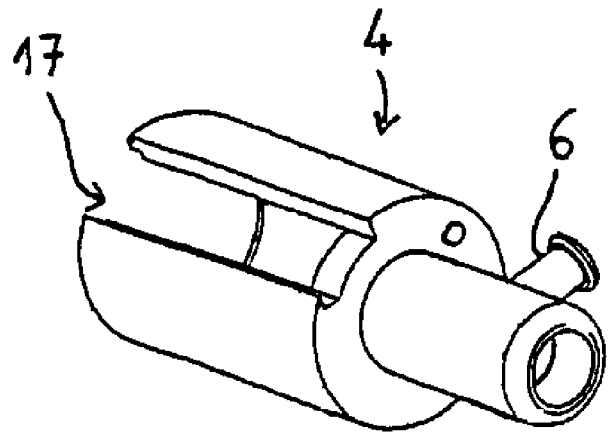

If slide 15 is added to body 4, body 4 has a cut-out 17 allowing assembly of the part forming the slide as can be seen on FIG. 7.

The cable fixed at the level of fastening zone 19 passes through an angle drive shown in the form of pulley 12 turning around a shaft 13 shown on FIG. 4.

The angle drive ensures tangential orientation of the cable so that it can be fixed at rotary shaft 9.

More precisely, shaft 9 has a groove 18 into which the other end of the cable is fastened.

On rotation of shaft 9, the cable winds or unwinds in groove 18.

The end of the cable is fixed in shaft 9 using a pin engaged through groove 18, for example by a hole 20.

It is easily understood that when the operator actuates gripping means 14 in the longitudinal direction of the valve, traction is applied on the cable which, by passing over pulley 12, exerts a rotational force on rotary shaft 9 and consequently, end 3 of flexible section 1.

As previously stated, the valve is advantageously configured so as to be closed by default.

In this context, means for returning to the default sealed position are executed.

In the example shown, this consists of a tension spring 24 which is oriented longitudinally in the direction of the valve and received around a guide element 23 in the form of a hollow cylinder with a central passage.

One of the ends of torsion spring 24 is fixed relative to body 4.

The other end acts in rotation with rotary shaft 9.

As can be seen on FIG. 4, body 4 includes a cavity 7 for receiving torsion spring 24 and its guide 23.

In addition, the circumference of cavity 7 forms a rotational guiding body for rotary shaft 9.

As an associated advantage, body 4 can be provided with a side opening 6, for example to allow the addition of a fluid such as an anticoagulant, a contrasting or washing medium.

Figure 10:
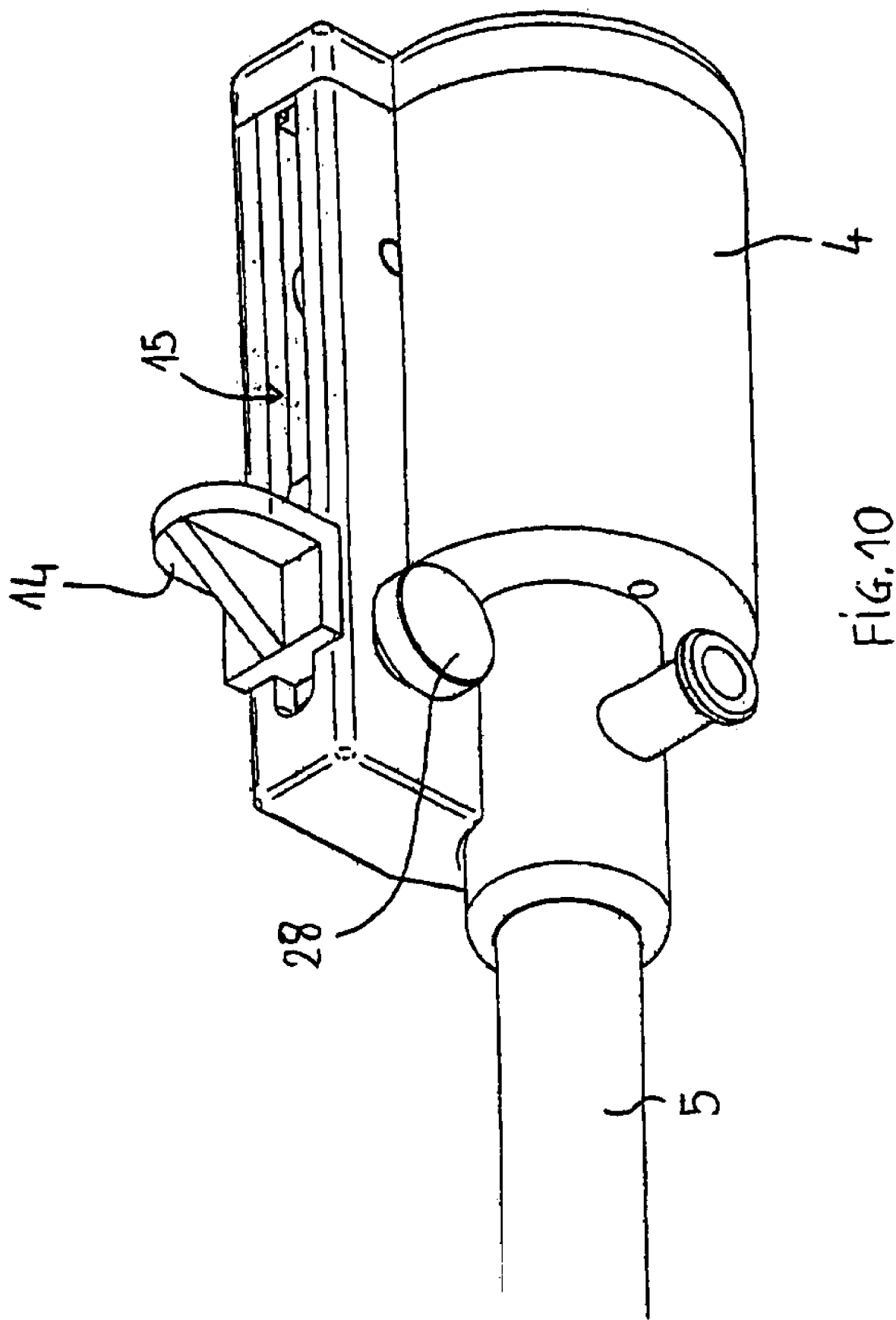
FIG. 10 is a perspective view of the invention.

In the example shown, and in particular such as can be seen on FIGS. 4, 5 and 10, means are shown for blocking the valve in the open position. Indeed, during a long period of non use, (in particular during storage), it is preferable for flexible section 1 not to be torsionally stressed to avoid its elastic properties deteriorating (in particular sticking if the flexible section is in silicone).

In the example shown, the blocking means include a pin 27 that can form a retaining stop for gripping means 14. In the position shown on FIG. 4, flexible section 1 is open whereas torsion spring 24 is tensioned.

It will be noted that the blocking means of the invention can be used with various types of rotational actuating means involving a cable or a gear system.

According to the example shown, and advantageously, gripping means that can operate the actuating means have a displacement which is appreciably in longitudinal direction 30 of the valve so as to maximize the ergonomy of the assembly. A system for transforming the movement is thus provided between gripping means 14 and end 3 which is mobile in rotation. In the example shown, the system for transforming the movement includes pulley 12 and the cable actuating rotary shaft 9. The transformation of movement can be produced by other actuating means.

According to the embodiment more precisely shown in FIGS. 11 to 15, a second cable 32 is created so as to transmit an opposite movement to the movement produced by the transmission cable. Thus, the operator is able to ensure the return movement of the valve by actuating it in the opposite direction to the first movement. In this case, return spring 24, which is present as an option in this case, accompanies the movement induced by additional cable 32.

Cable 32 has the advantage of ensuring a return to the optimal position without requiring the oversizing of return spring 24, and by countering any effects due to sticking or remnant deformation of the material used for flexible section 1.

Figure 11:
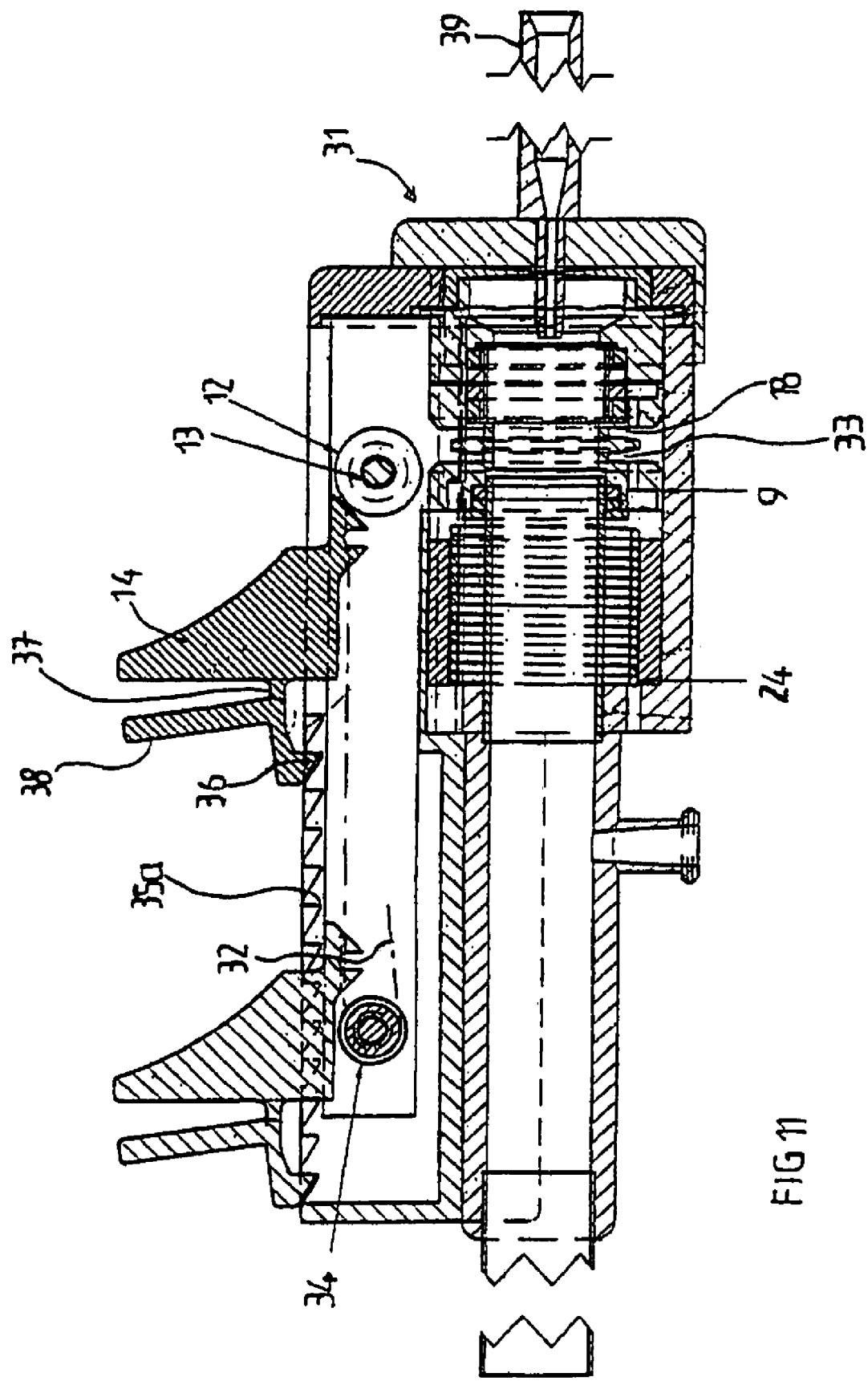
FIG. 11 is another embodiment of the invention with a system of two opposite cables.
Figure 12:
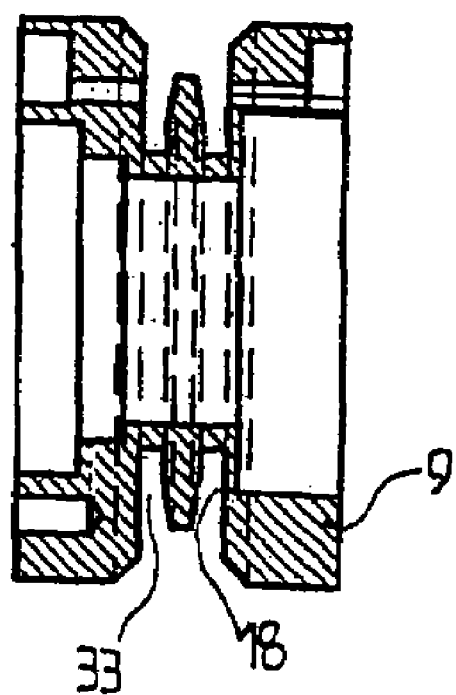
Figure 13:
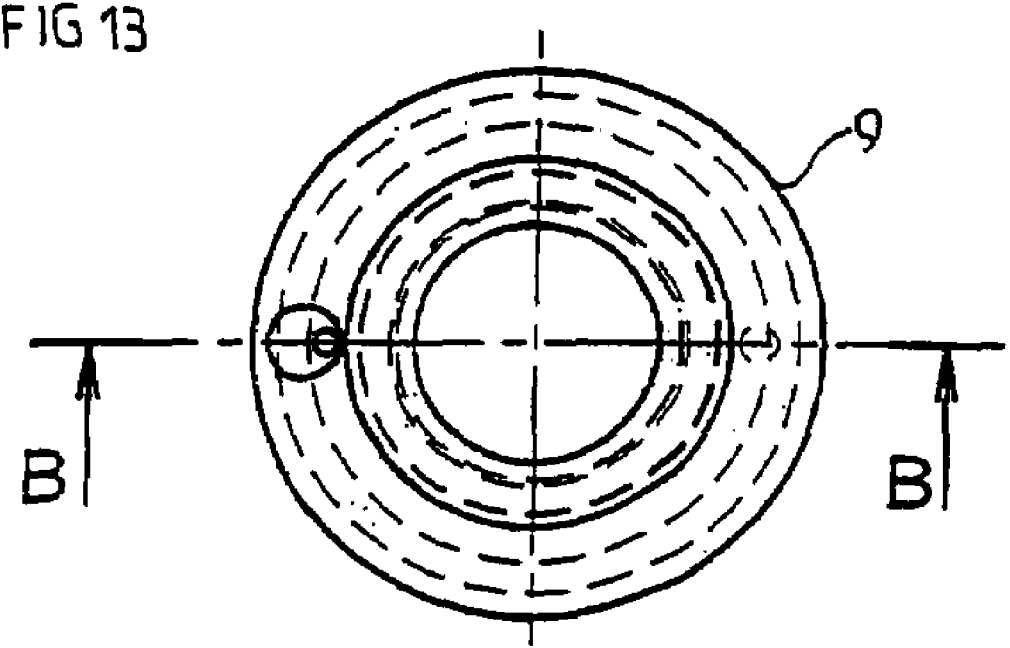
FIG. 13 shows a front view of a rotary shaft that can be used in this embodiment and FIG. 12 a sectional view.

From FIG. 11, it will be understood that the additional cable 32, which is partly illustrated, begins at a seat 40a or 40b for fastening the end of the cable on gripping means 14 and passes through return pulley 34 and an angle drive pulley common to the transmission cable or coaxial with it.

The other end of complementary cable 32 is fastened and wound in a groove 33 also formed of a rotary shaft 9. The cables are of course wound in grooves 18 and 33 so that the rotation of rotary shaft 9 simultaneously generates winding up of one and unwinding of the other.

FIG. 15 shows another advantageous characteristic of the invention which can be implemented in addition to the preceding characteristics or separately from them. This characteristic involves the formation of rows of teeth 35a, 35b on each edge of slide 15 in which gripping means 14 slide. By forming a finger 36, attached by an elastically deformable zone 37 to gripping means 14, gripping means 14 can be accurately positioned and consequently the desired degree of valve opening. The teeth have a sloping face to allow finger 36 to slide and a vertical face for blocking finger 36.

This toothed system, or another system which blocks gripping means 14, enables the user to apply a high force on the transmission cable (or complementary cable 32) and to maintain this force in order to obtain forced torsion of flexible section 1. This can produce a maximum seal even if the object to be introduced has a variable diameter: as the torsion is forced, flexible section 1 adapts to any reduction of the object diameter.

According to a non-illustrated variant, the edges of slide 15 are graduated or carry quantified indications on the degree of rotation of mobile end 3 or on the degree of seal. On this latter point, it should be noted that surgical instruments introduced are generally of a standard diameter (in general 3 or 4 different diameters) so that when the diameter of the object to be introduced is known the degree of seal can be deduced (for example expressed in French size) from the position of gripping means 14 in the slide.

The graduations shown on the slide may however also be limited to identifying the rotational diameter of mobile end 3. For example, it is useful to identify at least one rotation of 360°.

It will be noted that the direction of actuation of the gripping means is not restrictive: according to a first case, means 14 are pushed towards the distal insertion end in order to open the valve. In a second case, pushing closes the valve.

Lastly, stiffener 39 located at proximal end 31 of the instrument enables the objects to be introduced through the valve by ensuring their perfect guidance centred on the valve axis.

REFERENCES

1. Flexible section
2. End
3. End
4. Body
5. Tube
6. Side opening
7. Cavity
8. Fixed ring
9. Rotary shaft
10a, 10b. Internal ring
11. Cover
12. Pulley
13. Shaft
14. Gripping means
15. Slide
16a, 16b. Groove
17. Cut-out
18. Groove
19. Securing zone
20. Hole
21. Front
22. Back
23. Guide
24. Torsion spring
25. Seal
26. Seal
27. Pin
28. Knob
29. Additional valve
30. Longitudinal axis
31. Proximal end
32. Additional cable
33. Additional groove
34. Return pulley 35a, 35b. Rows of teeth
36. Finger
37. Elastic zone
38. Leg
39. Stiffener
40a, 40b. Seat of cable end

The invention claimed is:

1. A valve for surgical or medical instruments comprising:
a passage that can be at least partially closed by torsional deformation of a flexible section (1) of the passage wall,
means for rotating a mobile end (3) of flexible section (1) in order to generate torsion,
an actuation means comprise a cable for transmitting movement to the mobile end (3) of flexible section (1), and
an angle drive device to deviate the transmission cable, the angle drive and gripping means (14) are arranged so that gripping means (14) can be moved along the longitudinal axis of the valve.

2. The valve according to claim 1, wherein one end of the transmission cable is secured to gripping means (14) which can be moved by an operator.

3. The valve according to claim 1, wherein the angle drive consists of a pulley (12).

4. The valve according to claim 1, wherein it has means for returning mobile end (3) to the default position.

5. The valve according to claim 4, wherein the return means consist of a torsional spring (24) the end of which is fixed and whose other end acts in rotation with mobile end (3) of flexible section (1).

6. The valve according to claim 4, wherein the return means are arranged so that the passage of the valve is closed by default.

7. The valve according to claim 1, wherein the valve includes means for blocking the valve in the open position.

8. The valve according to claim 7 wherein the blocking means include a pin (27) blocking the actuating means.

9. The valve according to claim 1, wherein the mobile end (3) acts in rotation with a rotational shaft (9) to which is fastened one end of the transmission cable.

10. The valve according to claim 9, wherein the rotary shaft (9) has a groove (18) for fastening and winding up the transmission cable.

11. The valve according to claim 1, further comprising:
an additional cable (32) which, when pulled, is capable of transmitting a movement to mobile end (3) of flexible section (1) in the opposite direction to that of the transmission cable.

12. The valve according to claim 11, wherein the additional cable (32) is guided by a return pulley (34) and an angle drive pulley.

13. The valve according to claim 11, wherein the mobile end (3) acts in rotation with rotary shaft (9) which has a groove (18) for fastening and winding up the transmission cable and an additional groove (33) for fastening and winding up additional cable (32).

14. The valve according to claim 2, wherein the gripping means (14) move in a slide (15) the edges of which have at least one row of teeth (35a, 35b) for retaining a finger assembled elastically on the gripping means.

15. A medical or surgical instrument comprising:
a valve according to claim 1.

16. The valve according to claim 2, further comprising:
an angle drive device to deviate the transmission cable.

17. The valve according to claim 3, wherein the angle drive and the gripping means (14) are arranged so that the gripping means (14) can be moved along the longitudinal axis of the valve.

18. The valve according to claim 2, wherein the valve has means for returning mobile end (3) to the default position.

19. A valve for surgical or medical instruments comprising:
a passage that can be at least partially closed by torsional deformation of a flexible section (1) of the passage wall,
means for rotating a mobile end (3) of flexible section (1) in order to generate torsion, and
an actuation means comprise a cable for transmitting movement to the mobile end (3) of flexible section (1), wherein the return means consist of a torsional spring (24) the end of which is fixed and whose other end acts in rotation with mobile end (3) of flexible section (1), and
an angle drive device to deviate the transmission cable, the angle drive and gripping means (14) are arranged so that gripping means (14) can be moved along the longitudinal axis of the valve.

* * * * *